(12) United States Patent
Lee et al.

(10) Patent No.: US 6,869,551 B2
(45) Date of Patent: *Mar. 22, 2005

(54) PRECIPITATION OF SOLID PARTICLES FROM DROPLETS FORMED USING FOCUSED ACOUSTIC ENERGY

(75) Inventors: David Soong-Hua Lee, Mountain View, CA (US); Richard N. Ellson, Palo Alto, CA (US); Theodore J. Williams, Mountain View, CA (US)

(73) Assignee: Picoliter Inc., Sunnyvale, CA (US)

( * ) Notice: Subject to any disclaimer, the term of this patent is extended or adjusted under 35 U.S.C. 154(b) by 326 days.

This patent is subject to a terminal disclaimer.

(21) Appl. No.: 10/244,128

(22) Filed: Sep. 13, 2002

(65) Prior Publication Data

US 2003/0012892 A1 Jan. 16, 2003

Related U.S. Application Data

(63) Continuation-in-part of application No. 10/112,693, filed on Mar. 28, 2002, now Pat. No. 6,642,061, and a continuation-in-part of application No. 09/823,899, filed on Mar. 30, 2001, now Pat. No. 6,596,206, and a continuation-in-part of application No. 09/823,890, filed on Mar. 30, 2001, now Pat. No. 6,610,223.

(51) Int. Cl.$^7$ ................................................. B29B 9/00
(52) U.S. Cl. ....................... 264/9; 264/5; 264/7; 425/6; 425/10
(58) Field of Search ........................ 264/5, 7, 9; 425/6, 425/10; 435/6, 10

(56) References Cited

U.S. PATENT DOCUMENTS

| | | |
|---|---|---|
| 3,986,669 A | 10/1976 | Martner |
| 4,089,801 A | 5/1978 | Schneider |
| 4,308,547 A | 12/1981 | Lovelady et al. |
| 4,697,195 A | 9/1987 | Quate et al. |
| 4,719,476 A | 1/1988 | Elrod et al. |
| 4,751,529 A | 6/1988 | Elrod et al. |
| 4,751,530 A | 6/1988 | Elrod et al. |
| 4,751,534 A | 6/1988 | Elrod et al. |
| 4,797,693 A | 1/1989 | Quate |
| 4,801,411 A | 1/1989 | Wellinghoff et al. |
| 4,801,953 A | 1/1989 | Quate |
| 4,812,856 A | 3/1989 | Wallace |
| 4,959,674 A | 9/1990 | Khri-Yakub et al. |
| 5,041,849 A | 8/1991 | Quate et al. |
| 5,087,931 A | 2/1992 | Rawson |

(List continued on next page.)

FOREIGN PATENT DOCUMENTS

| | | |
|---|---|---|
| DE | 19752585 A1 | 6/1999 |
| EP | 0434931 A2 | 7/1991 |
| EP | 0542314 | 7/1998 |
| WO | WO 00/12278 | 3/2000 |
| WO | WO 00/17413 | 3/2000 |
| WO | WO 00/37169 | 6/2000 |
| WO | WO 00/44468 | 8/2000 |
| WO | WO 02/00200 | 1/2002 |

OTHER PUBLICATIONS

U.S. appl. No. 09/669,194, filed Sep. 25, 2000, Ellson et al.
U.S. appl. No. 09/669,996, filed Sep. 25, 2000, Ellson et al.
U.S. appl. No. 09/669,997, filed Sep. 25, 2000, Mutz et al.

(List continued on next page.)

*Primary Examiner*—Mary Lynn Theisen
(74) *Attorney, Agent, or Firm*—Dianne E. Reed; Reed IP Law Group

(57) ABSTRACT

Methods and devices are disclosed that use focused acoustic energy to generate solid particles containing at least one compound of interest. Focused acoustic radiation serves to eject droplets containing a compound of interest dissolved in a solvent. The droplets are subjected to a condition that allows for the compound of interest to precipitate out of solution, thereby generating solid particles. The particles are typically of controlled size, composition, and/or structure. Often, particles of substantially identical size are generated.

83 Claims, 3 Drawing Sheets

U.S. PATENT DOCUMENTS

| | | |
|---|---|---|
| 5,122,818 A | 6/1992 | Elrod et al. |
| 5,216,451 A | 6/1993 | Rawson et al. |
| 5,229,016 A | 7/1993 | Hayes et al. |
| 5,229,793 A | 7/1993 | Hadimioglu et al. |
| 5,231,426 A | 7/1993 | Sweet |
| 5,339,101 A | 8/1994 | Rawson et al. |
| 5,377,902 A | 1/1995 | Hayes |
| 5,392,064 A | 2/1995 | Hadimioglu et al. |
| 5,415,679 A | 5/1995 | Wallace |
| 5,436,327 A | 7/1995 | Southern et al. |
| 5,498,444 A | 3/1996 | Hayes |
| 5,520,715 A | 5/1996 | Oeftering |
| 5,556,752 A | 9/1996 | Lockhart et al. |
| 5,591,490 A | 1/1997 | Quate |
| 5,608,433 A | 3/1997 | Quate |
| 5,629,724 A | 5/1997 | Elrod et al. |
| 5,631,678 A | 5/1997 | Hadimioglu et al. |
| 5,643,353 A | 7/1997 | Wallace et al. |
| 5,658,802 A | 8/1997 | Hayes et al. |
| 5,669,971 A | 9/1997 | Bok et al. |
| 5,722,479 A | 3/1998 | Oeftering |
| 5,744,305 A | 4/1998 | Fodor et al. |
| 5,798,779 A | 8/1998 | Nakayasu et al. |
| 5,808,636 A | 9/1998 | Stearns |
| 5,874,029 A | 2/1999 | Subramaniam et al. |
| 6,010,316 A | 1/2000 | Haller et al. |
| 6,015,880 A | 1/2000 | Baldeschwieler et al. |
| 6,028,189 A | 2/2000 | Blanchard |
| 6,029,896 A | 2/2000 | Self et al. |
| 6,110,426 A | 8/2000 | Shalon et al. |
| 2002/0000681 A1 | 1/2002 | Gupta et al. |
| 2002/0037359 A1 | 3/2002 | Mutz et al. |
| 2002/0037579 A1 | 3/2002 | Ellson et al. |
| 2002/0073989 A1 | 6/2002 | Hadimioglu |
| 2002/0073990 A1 | 6/2002 | Noolandi et al. |
| 2002/0077369 A1 | 6/2002 | Noolandi et al. |

OTHER PUBLICATIONS

U.S. appl. No. 09/823,890, filed Mar. 30, 2001, Lee.

U.S. appl. No. 09/823,899, filed Mar. 30, 2001, Lee.

Amemiya et al. (1997), *Proceedings of the 1997 IS&T's NIP 13: 1997 International Conference on Digital Printing Technologies,* pp. 698–702.

Chattopadhyay et al. (2001), "Production of Griseofulvin Nanoparticles Using Supercritical CO2 Antisolvent with Enhanced Mass Transfer," *International Journal of Pharmaceutics 228* :19–31.

Debenedetti et al. (1993), "Application of Supercritical Fluids for the Production of Sustained Delivery Devices," *Journal of Controlled Release 24* :27–44.

Elrod et al. (1989), "Nozzleless Droplet Formation with Focused Acoustic Beams," *J. Appl. Phys. 65* (9):3441–3447.

Hadimioglu et al. (1992), "Acoustic Ink Printing," *Ultrasonics Symposium,* pp. 929–935.

Jung et al. (2001), "Particle Design Using Supercritical Fluids: Literature and Patent Survey," *Journal of Supercritical Fluids 20:* 179–219.

MacBeath et al. (2000), "Printing Proteins as Microarrays for High–Throughput Function Determination," *Science 289:* 1760–1763.

Steel et al. (2000), "The Flow–Thru Chip™: A Three–Dimensional Biochip Platform," *Microarray Biochip Technology,* Chapter 5, pp. 87–117, BioTechniques Books, Natick, MA.

Tom et al. (1991), "Formation of Bioerodible Polymeric Microspheres and Microparticles by Rapid Expansion of Supercritical Solutions," *Biotechnol. Prog. 7*(5):403–411.

PRECIPITATION OF SOLID PARTICLES FROM DROPLETS FORMED USING FOCUSED ACOUSTIC ENERGY

CROSS-REFERENCE TO RELATED APPLICATIONS

This is a continuation-in-part of U.S. patent application Ser. Nos. 09/823,899 and 09/823,890, both filed Mar. 30, 2001, now U.S. Pat. Nos. 6,596,206 and 6,610,223, respectively, and U.S. patent application Ser. No. 10/112, 693, filed Mar. 28, 2002, now U.S. Pat. No. 6,642,061, the disclosures of which are incorporated herein by reference.

TECHNICAL FIELD

This invention relates generally to controlled generation of particles containing at least one compound of interest. In particular, the invention relates to the use of focused acoustic energy for generating solid particles of controlled size, composition, and/or structure from a solution containing the compound of interest. The invention may be employed to generate particles containing one or more pharmaceutical agents.

BACKGROUND

Solid particles, particularly small particles of controllable size and composition, find utility in a variety of industries. Among other advantages, particles of controlled size and composition provide for greater consistency and predictability in handling and use. For example, small particles of substantially identical size possess favorable flow characteristics and exhibit little variation in interparticle behavior. When such particles are used in conjunction with a chemical process, uniformity in particle size allows the particles to behave and function consistently, an attribute that is especially advantageous for the pharmaceutical industry, where the particle size of a therapeutic agent can affect the dissolution rate, bioavailability, and overall stability of the agent.

Pulmonary drug delivery relies on inhalation of a drug dispersion or aerosol by a patient so that the active agent within the dispersion can reach the alveoli of the lungs for absorption into blood circulation. As discussed in U.S. Pat. No. 5,740,794 to Smith et al., pulmonary delivery is well suited for the delivery of proteins and polypeptides, which are sometimes difficult to deliver by other routes of administration. In particular, protein and polypeptide drugs may be readily formulated as dry powders, since many otherwise labile proteins and polypeptides can be stably stored as lyophilized or spray-dried powders by themselves or in combination with suitable particulate carriers.

Since drug release rate is directly related to the surface area and size of a particle containing the drug, precise control of the particle size is particularly important in regulating the rate of drug release. In addition, the dosage of many protein and polypeptide drugs must be precisely controlled in order to deliver the intended amount of drug for efficacy without overdosing. As proteins and polypeptides are typically more costly than conventional drugs, the ability to efficiently deliver a dry powder to the target region of the lungs with a minimal loss of drug is economically desirable.

Pulmonary delivery of a powdered therapeutic agent requires specifically sized particles, generally having a diameter on the order of about 1 $\mu$m to about 7 $\mu$m. Particles that are too large tend to be deposited within the throat, while particles that are too small may be exhaled. In either case, the therapeutic agent is misdirected and does not reach the target region of the lungs. Thus, a critically important consideration in the development of particulate pharmaceutical products is the ability to produce uniform particles of an appropriate size that contain a therapeutic agent.

It should be noted that optimal particle size for rapid drug absorption through alveolar membranes to bring about a desired pharmacokinetic effect is on the order of 100 nm or smaller. Particles having a size of less than about 1 $\mu$m tend to drift, often do not reach the alveolar membrane, and may be transported out of the body when a patient exhales. It would be desirable, therefore, to be able to inexpensively create pharmaceutical particles on the size scale of about 10 nm to 100 nm, which would be attached to larger carrier particles of about 5 $\mu$m. Such amalgamated particles would be particularly suited for rapid and efficient pulmonary delivery.

Various approaches for attaining small and uniform particles have been employed. Conventional comminution techniques, e.g., crushing, grinding and milling, rely on mechanical forces to break apart relatively large particles into smaller particles. When grinding and/or milling media are used, there is a potential for contamination. Other drawbacks to mechanical comminution techniques include, for example, the potential for damage to proteins and other therapeutic biomolecules, as well as the wide variation in particle size produced by such techniques. Large variations in particle size also limit the ability to produce sustained-release formulations and result in the waste of therapeutic agents. Although it is possible to sort comminuted particles to provide a more narrow particle size distribution, large quantities of particles not having the desired size are eliminated. In addition, the process of sorting represents another potential source of contamination.

Alternatively, pharmaceutical particles of a controlled size may be produced using conventional precipitation/crystallization methods. In such methods, the therapeutic agent is initially dissolved in a suitable solvent. In one approach, the temperature of the solution is changed so that the solubility of the solute is decreased. In another approach, a second solvent, an "antisolvent," is added so that the solubility of the solute is decreased. In both approaches, the solute precipitates or crystallizes out of the solution due to reduced solubility in the altered solution. These methods, however, often require toxic solvents, result in wet particles (that require further processing, e.g., drying), and may also produce particles with considerable size variation.

In some instances, supercritical fluid technology, such as the rapid expansion of supercritical solutions (known as the "RESS" method), is employed. Although use of supercritical fluid technology enables the production of relatively small particles of uniform size, such methods are not without drawbacks. One problem associated with supercritical fluid handling methods is their reliance on nozzles and tubes for delivering the solutions. Nozzles are known to wear down over time, thus altering the geometry of the equipment and affecting the size of the droplets formed. Also, nozzles may become blocked during use, when, for example, particles agglomerate upon rapid expansion within the nozzle bore. In addition, nozzles and associated components require cleaning and may contaminate solutions when not properly maintained. Furthermore, the resulting droplet sizes are relatively varied for both supercritical and conventional solutions that are produced by methods relying on nozzles, leading to a large variance in surface tension between the differently sized droplets. At the droplet sizes required for supercritical methods, the differences in surface tension between droplets can cause wide variations in crystallization kinetics and growth, leading to the formation of differently sized particles. U.S. Pat. No. 5,874,029 to Subramaniam et al. describes methods for producing small-sized droplets using nozzles; however, these methods are still unable to effectively and consistently produce droplets of uniform size.

Nozzleless approaches to formation of liquid droplets containing pharmaceutical agents have been described. U.S. Patent Application Publication No. 20020077369 to Noolandi et al., for example, describes focused acoustics to generated liquid droplets from a single bulk fluid near an airway for direct inhalation. The focused acoustic energy may be used in two ways: either to generate liquid droplets whose diameter is on the order of the acoustic wavelength as described in U.S. Pat. No. 4,308,547 to Lovelady et al. or alternatively by capillary wave generation using shorter bursts as described in U.S. Patent Application Publication No. 20020073989 to Hadimioglu. Formation of solid particles by these nozzleless approaches is not described.

Thus, there is a need in the art for improved particle formation techniques, wherein particle formation is highly reproducible, controllable, and predictable. An ideal method would minimize or eliminate contact of the particle-forming fluid(s) with processing equipment surfaces or contaminants adsorbed thereon. The present invention addresses the aforementioned need in the art by using focused acoustic energy to eject particle-forming droplets from a solution containing a compound of interest as a solute, and by subjecting the droplets to conditions that allow the compound to precipitate out of solution.

SUMMARY OF THE INVENTION

Accordingly, it is a primary object of the invention to address the aforementioned need in the art by providing methods and devices that use focused acoustic ejection technology to produce droplets containing a solution, which are then subjected to a condition effective to allow a compound of interest to precipitate out of solution.

Additional objects, advantages, and novel features of the invention will be set forth in part in the description which follows, and in part will become apparent to those skilled in the art upon examination of the following, or may be learned through routine experimentation in the practice of the invention.

In a first embodiment, the invention relates to a method for generating solid particles of substantially identical size. The method involves first providing a reservoir containing a solution of a compound of interest dissolved in a solvent. Focused acoustic radiation is repeatedly applied to the solution in a manner effective to eject from the reservoir a plurality of droplets, each of which contains the solution. The droplets are then subjected to a condition that allows for the compound of interest to precipitate out of solution, thereby generating solid particles of substantially identical size. In some instances, focused acoustic radiation is applied to the solution in the reservoir at a plurality of loci so as to eject droplets therefrom. The resulting particles may be formed either in succession or simultaneously.

In another embodiment, the invention relates to a method for generating a solid particle coated with a compound of interest. This method also involves providing a reservoir as above, except that the reservoir additionally contains a discrete localized volume having a composition different from the composition of the solution. Focused acoustic radiation is applied, and a droplet is ejected from the reservoir, wherein the droplet contains the discrete localized volume and the solution. By subjecting the droplet to a condition that allows the compound of interest to precipitate out of solution onto the localized volume, a solid particle is formed, which is coated with the compound of interest.

In still another embodiment, the invention relates to a method for generating a solid particle comprised of different compounds of interest. A reservoir is provided containing immiscible fluids, wherein each fluid contains a different compound of interest, and at least one compound of interest is dissolved in a solvent. In some instances, each fluid is comprised of a solution containing a different compound of interest as a solute in a solvent. In other instances, the compound of interest contained in at least one fluid is not a solute in a solvent. Focused acoustic radiation is then applied to at least one of the fluids in a manner effective to eject from the reservoir a droplet comprised of the immiscible fluids. The droplet is then subjected to a condition that allows the at least one dissolved compound to precipitate out of solution, thereby generating the solid particle.

When immiscible fluids are employed, they are typically contained in the reservoir as layers. Through appropriate selection of fluids, use of focused acoustic radiation, and ideal precipitation conditions, solid particles are formed that comprise an outer region encapsulating a core region. Either the outer region or core region may be formed as a result of the precipitation a compound of interest. Typically, the outer region occupies no more than about 50% of the total particle volume.

In yet another embodiment, the invention relates to a method for generating at least one solid particle, each containing a compound of interest. The method involves providing a reservoir containing a solution of a compound of interested dissolved in a solvent, and applying focused acoustic energy in a manner effective to eject a droplet from the reservoir. The droplet is subjected to a condition that allows the compound to precipitate from solution at a plurality of loci. As a result, one or more solid particles are generated.

For any of the above embodiments, a compound of interest may be precipitated from an ejected droplet by any of a number of means. For example, the droplet may be exposed to an antisolvent, then heated and/or cooled. In some instances, the compound may be polymerized and/or reacted with another compound in the droplet. In any case, the particles generated may be substantially free of solvent or they may contain a fluid. As a result, the composition and structure of the particle generated may be controlled.

The invention is particularly suited for forming solid particles that contain one or more pharmaceutical agents, such as diagnostic agents, pharmacologically active agents, or excipients. In particular, the invention is well suited to generate particles for pulmonary delivery. Thus, additional exemplary pharmaceutical agents suitable for use with the present invention include respiratory drugs such as anti-inflammatory corticosteroids, bronchodilators, and mixtures thereof. For pulmonary delivery, the size of the particles may be in the range of about 0.1 nm to about 10 $\mu$m.

In a further embodiment, the invention provides a system for generating solid particles of a plurality of compounds of interest. A reservoir is provided containing a solution of a first compound of interest as a solute in a solvent and a second compound of interest. Also provided is an acoustic ejector comprising an acoustic radiation generator for generating acoustic radiation and a focusing means for focusing the acoustic radiation at a focal point within the solution in the reservoir so as to eject a droplet therefrom. The ejector is positioned in acoustic coupling relationship to the reservoir. Typically, the focusing means has an F-number of no more than 2 or 1. In addition, the second compound of interest is contained in a fluid that is immiscible with the solution and/or in a discrete localized volume within the solution. Optionally, a means is provided for subjecting the droplet to a condition that allows the first compound of interest to precipitate out of solution.

DETAILED DESCRIPTION OF THE INVENTION

Figure 1:
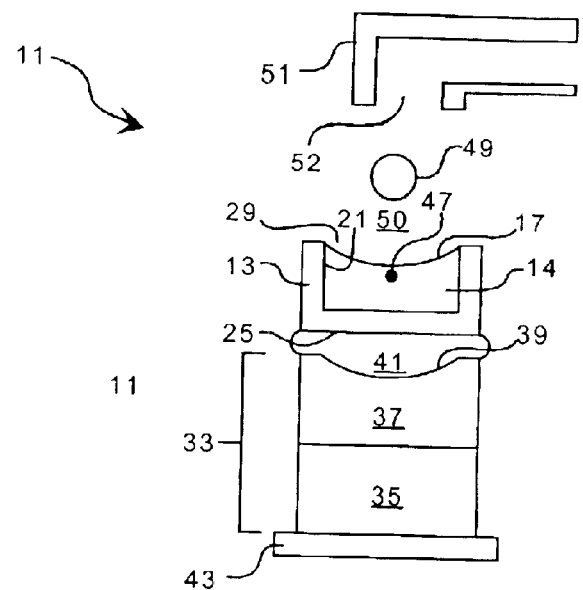
FIG. 1 is a schematic cross-sectional view of a focused acoustic energy device of the invention using a single ejector in conjunction with the preparation of particles containing a compound of interest.

Before describing the present invention in detail, it is to be understood that, unless otherwise indicated, this invention is not limited to specific pharmaceutical agents, fluids, acoustic ejection devices, or the like, as such may vary. It is also to be understood that the terminology used herein is for the purpose of describing particular embodiments only, and is not intended to be limiting.

It must be noted that, as used in this specification and in the appended claims, the singular forms "a," "an," and "the" include plural referents unless the context clearly dictates otherwise. Thus, for example, the term "a solvent" is intended to mean a single solvent or a mixture of a solvent with one or more cosolvents, "a pharmaceutical agent" refers to a single pharmaceutical agent as well as to a mixture of different pharmaceutical agent, "a reservoir" is intended to mean one or more reservoirs, and the like.

In describing and claiming the present invention, the following terminology will be used in accordance with the definitions set out below.

The terms "acoustic coupling" and "acoustically coupled" used herein refer to a state wherein a first entity is placed in direct or indirect contact with another entity so as to allow acoustic radiation to be transferred between the objects without substantial loss of acoustic energy. When two entities are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The terms "acoustic radiation" and "acoustic energy" are used interchangeably herein and refer to the emission and propagation of energy in the form of sound waves. As with other waveforms, acoustic radiation may be focused using a focusing means, as discussed below. Although acoustic radiation may have a single frequency and associated wavelength, acoustic radiation may take a form, e.g. a "linear chirp," that includes a plurality of frequencies. Thus, the term "characteristic wavelength" is used to describe the mean wavelength of acoustic radiation having a plurality of frequencies.

The term "antisolvent" refers to a fluid that, when mixed with a solvent in which a solute is dissolved, reduces the capacity of the solvent to dissolve the solute. Thus, when an antisolvent is admixed with a solution of a solute in a solvent, the solubility of the solute can be reduced to the point at which it precipitates out of solution. Gases (particularly compressed gases) can act as antisolvents, although the preferred antisolvents herein are in a supercritical fluid state. The antisolvent must be sufficiently miscible with the solvent so that solute precipitation does in fact occur. It should be appreciated that miscibility can be controlled by varying one or more parameters within the solvent/antisolvent system, for example, the solvent and antisolvent system may be maintained at a sufficiently low temperature so that the two fluids are not particularly miscible (e.g., for storage purposes); and later, the temperature may be raised so that the two fluids are miscible and particle formation can occur.

The terms "biomolecule" and "biological molecule" are used interchangeably herein to refer to any organic molecule—whether naturally occurring, recombinantly produced, or chemically synthesized in whole or in part—that is, was, or can be a part of a living organism. The terms encompass, for example, nucleotides, amino acids, and monosaccharides, as well as oligomeric and polymeric species such as oligonucleotides and polynucleotides, peptidic molecules such as oligopeptides, polypeptides and proteins, saccharides such as disaccharides, oligosaccharides, polysaccharides, mucopolysaccharides or peptidoglycans (peptidopolysaccharides), and the like. The term also encompasses ribosomes, enzyme cofactors, pharmacologically active agents, and the like.

The term "encapsulate" as in "a first fluid encapsulating a second fluid" refers to a situation wherein the second fluid is enclosed within the first fluid. Similarly, "a compound of interest encapsulating a solid particle" refers to a situation wherein the solid particle is coated with and/or enclosed by a compound of interest. The term "encapsulate" is typically used in a three-dimensional context. For example, a droplet floating freely in space, i.e., one that is not in contact with a solid surface, may be formed from one fluid "encapsulating" another.

The term "fluid" as used herein refers to matter that is nonsolid, or at least partially gaseous and/or liquid. A fluid may contain a solid that is minimally, partially, or fully solvated, dispersed, or suspended. Examples of fluids include, without limitation, aqueous liquids (including water per se and salt water) and nonaqueous liquids such as organic solvents, lipidic liquids, supercritical fluids, and the like. As used herein, the term "fluid" is not synonymous with the term "ink" in that ink must contain a colorant and may not be gaseous.

The terms "focusing means" and "acoustic focusing means" as used herein refer to a means for causing acoustic waves to converge at a focal point by either a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as known in the art and described, for example, in U.S. Pat. No. 5,798,779 to Nakayasu et al. and Amemiya et al. (1997) *Proceedings of the 1997 IS&T NIP 13 International Conference on Digital Printing Technologies*, pp. 698–702.

The term "immiscible" is used in its conventional sense to refer to two fluids that are less than completely miscible, in that mixing two such fluids results in a mixture containing more than one fluid phase. It is preferred that two "immiscible" fluids as provided herein be completely or almost completely immiscible, i.e., that they give rise to a mixture containing two phases, wherein each phase contains at least about 95%, preferably at least about 99%, of a single fluid. In addition, the term is intended to encompass situations wherein two fluids in contact remain in separate phases over an extended period of time but eventually do mix. That is, such fluids are "kinetically immiscible." In such a case, it is preferred that such fluids remain as separate phases for at least 10 minutes, more preferably for at least an hour, and optimally for over 24 hours.

"Optional" or "optionally" means that the subsequently described circumstance may or may not occur, so that the description includes instances where the circumstance occurs and instances where it does not.

The terms "pharmaceutical agent," "active agent," and "drug" are used interchangeably herein to refer to a chemical material or compound that, when administered to an organism (human or animal), induces a desired pharmacological effect, including a therapeutic effect, a prophylactic effect, and/or a diagnostic effect.

By "pharmaceutically acceptable carrier" is meant a material or materials that are suitable for drug administration and are not biologically or otherwise undesirable, i.e., materials that may be administered to an individual along with an active agent such that the combination does not cause any undesirable biological effects or interact in a deleterious manner with any of the other components of the pharmaceutical formulation in which it is contained. Typically, the term is synonymously used the term "excipient" when used in the context of drug delivery.

Similarly, a "pharmacologically acceptable" salt, ester, or other derivative of an active agent as provided herein is a salt, ester, or other derivative that is not biologically or otherwise undesirable.

The terms "precipitate" and "precipitation" are used herein in their ordinary sense and refer to the separation of a compound via a phase change from a solution that contains the compound as a solute. This separation typically results by the action of some reagent added to the solution, or as a consequence of some force, such as heat, cold, or mechanical agitation. For example, precipitation may involve the nucleation and growth of a crystalline compound from a solution that contains the compound dissolved in a solvent.

The term "reservoir" as used herein refers to a receptacle or chamber for holding or containing a fluid. Thus, a fluid in a reservoir necessarily has a free surface, i.e., a surface that allows a droplet to be ejected therefrom.

The term "solid" is used herein in its ordinary sense and refers to a state of matter having a definite shape and volume. For example, the term "solid particle" is used herein to refer to a particle that is at least partially solid in nature, wherein at least the solid portion has a definite shape and volume. Typically, the term is employed to refer to matter that is at least 50% solid by volume. Preferably, solid particles are at least 90 percent solid by volume. Hollow particles are not excluded from the term "solid" as long as the particle is at least partially solid. Similarly, a solid particle may be formed in part from a gel or an extremely viscous liquid.

The terms "solid particle," "particle," "powder," and "particulate" are used interchangeably herein to refer to solid matter that is small in size. Generally, the average size of the particles prepared using the method of the invention is in the range of about 0.1 nm to about 5 µm in diameter, more typically in the range of about 5 nm to about 2.5 µm in diameter. A "droplet" is distinguishable from a particle in that droplets do not require the presence of a solid.

The term "solvent" refers to a fluid that is capable of at least partially dissolving a compound of interest as a solute.

The term "substantially" as in, for example, the phrase "particles of substantially identical size," refers to particles that differ in size by no more than 20%, preferably no more than 10%, more preferably no more than 5%, and most preferably no more than 1%. Other uses of the term "substantially" involve an analogous definition.

The term "supercritical fluid" refers to a fluid at or above both its critical pressure $P_c$ and critical temperature $T_c$. The molar volume and solubilizing capacity of a supercritical fluid can be substantially altered by varying the temperature and/or pressure of the fluid. Fluids that are kept slightly below their actual critical temperature and pressure can exhibit similar characteristics; thus, the term "supercritical fluid" is intended to encompass such fluids as well.

The invention accordingly provides methods that generate particles containing at least one compound of interest, wherein the particles are of controlled size, composition, and/or structure. A reservoir is provided containing a solution of a compound of interested dissolved in a solvent. Focused acoustic radiation is applied to the solution in a manner effective to eject a droplet containing the solution. The droplet is then subjected to a condition that allows for the compound of interest to precipitate out of solution, thereby generating an individual solid particle.

The invention provides improved control over the size, composition, and structure of the particle produced, typically resulting in the generation of particles of substantially identical size. For example, the method may be used to produce particles having a size of about 5 µm with relatively tight size distributions, e.g., standard deviations of only a few percentage points. See Elrod et al. (1989) "Nozzleless Droplet Formation with Focused Acoustic Beams," *J. Appl. Phys.* 65(9):3441–3447. In addition or in the alternative, the droplet is subjected to a condition that allows the compound to precipitate from solution at a plurality of loci in order to generate one or more solid particles. In any case, the invention may be used to generate a solid particle coated with a compound of interest, achieved by providing a reservoir as above except that the solution additionally contains a discrete localized volume having a composition different from the composition of the solution. By ejecting a droplet containing the localized volume and subjecting the droplet to a condition that allows the compound of interest to precipitate out of solution onto the localized volume, a solid particle is formed coated with the compound of interest. Similarly, the reservoir may be provided containing immiscible fluids, wherein each fluid contains a different compound of interest and at least one compound of interest is dissolved in a solvent. As a result, the ejected droplet is comprised of the immiscible fluids. By allowing the dissolved compound or compounds to precipitate out of solution, a solid particle comprised of different compounds of interest is generated.

The inventive method may be employed to generate a plurality of particles in succession or simultaneously. For example, a reservoir may be provided such that a single droplet at a time is ejected therefrom, and a single particle may be formed from each ejected droplet. In the alternative, focused acoustic radiation may be applied to the solution in the reservoir at a plurality of loci so as to eject droplets therefrom, and the droplets are subjected to conditions that allow the compound to precipitate out of solution. The droplets may be ejected from the loci simultaneously or in succession.

In general, it is preferred that the solution from which the droplet is ejected is substantially saturated with the compound of interest, thus allowing for rapid precipitation of the compound of interest. In addition, there are a number of ways in which a compound of interest may be precipitated from an ejected droplet. For example, the droplet may be exposed to an antisolvent. The solution will generally be saturated or near saturated, such that supersaturation occurs when a solution droplet contacts and admixes with the antisolvent. As a result, solid particles are formed from the nucleation and growth of the compound of interest as a precipitate. Gaseous and supercritical fluids are particularly preferred as antisolvents. For many pharmaceutical agents, it is desirable to use an antisolvent fluid that permits processing at relatively mild temperatures. For processing of proteins and polypeptides, in particular, the antisolvent fluid should preferably exhibit a critical temperature of from about 0° C. to about 50° C. Exemplary preferred antisolvent fluids include carbon dioxide and nitrogen.

As changes in temperature typically alter the capacity of a solvent to dissolve compounds, a compound of interest may be precipitated from a droplet upon heating and/or cooling. Similarly, exposing a droplet to reduced pressure may also induce the compound of interest to precipitate and/or crystallize from solution. In some instances, the compound may be polymerized and/or reacted with another compound in the droplet. In any case, the particles generated may be either substantially free of solvent or they may contain a fluid.

The invention may be used to form solid particles containing one or more compounds of interest. Any of the compounds of interest discussed in U.S. application Ser. No. 09/823,890, "Focused Acoustic Energy in the Generation of Solid Particles," inventor Lee, filed Mar. 30, 2001, may be contained therein. In some embodiments, the invention may be used to form solid particles containing biomolecules, e.g., DNA, RNA, oligonucleotides, polynucleotides, peptides, oligopeptides, polypeptides and proteins (including fluorescent proteins), ribosomes, and enzyme cofactors such as biotin. Biomolecules (as well as other agents) may be radioactively tagged or otherwise labeled for diagnostic purposes. In some instances, the compound of interest may be a diagnostic agent. For pharmaceutical and other selected applications, the size of the solid particle formed by the inventive method is typically in the range of about 0.1 nm to about 10 µm. Preferably, the size of the solid particle formed is in the range of about 2 µm to about 7 µm.

In addition, the particles formed may contain pharmaceutical agents such as those discussed in U.S. patent application Ser. No. 09/823,899, "Generation of Pharmaceutical Agent Particles Using Focused Acoustic Energy," inventor Lee, filed Mar. 30, 2001. For example, the pharmaceutical agent may be any known or hereafter discovered pharmacologically active agent, and may be a compound that occurs in nature, a naturally occurring compound that has been chemically modified, or a compound that has been chemically synthesized. Since the invention is used for manufacturing particles and powders, the primary pharmaceutical agent candidates will be those that are suitable for administration of particulate dosage forms, e.g., those used for inhalation therapy, as in, for example, a dry powder inhaler. Delivery of pharmaceutical particles via the respiratory system is of increasing interest in the pharmaceutical field, particularly for those active agents that are problematic when administered orally, e.g., by causing gastrointestinal distress and/or possessing variable rates of absorption and metabolism. In addition, respiratory drugs such as anti-inflammatory corticosteroids, bronchodilators, and mixtures thereof are particularly suited or desirable for pulmonary delivery.

The particulates prepared using the inventive method may include components other than the active agent. In order to incorporate these extra components, additional compounds of interest may be added to the agent-containing solvent prior to droplet ejection. For example, a dry powder composition for pulmonary administration may include a pharmaceutically acceptable carrier such as a mono-, di-, or polysaccharide, and the carrier may be dissolved in the solvent along with the pharmaceutical agent prior to droplet ejection and particle formation. Other additives commonly included in particulate pharmaceuticals include diluents, stabilizers, surfactants, lubricants, etc., which may be incorporated into the pharmaceutical particles prepared herein in an analogous manner, as discussed in detail in U.S. patent application Ser. No. 09/823,899. In some instances, biological materials may be included as well. Such materials may be extracted from animals, plants microbes or other organisms. For example, additives may include membrane lipids such as sphingomyelin, phosphatidylethanolamine, phosphatidylcholine, and combinations thereof. In some cases, such biological materials and extracts may be used to solublized and/or stablize a compound of interest such as a pharmaceutical agent.

Depending on the hydrophilicity of the pharmaceutical agent, suitable solvents for the pharmaceutical agent will be either hydrophilic or lipophilic. Hydrophilic agents will of course, dissolve in aqueous solvents and other hydrophilic solvents, while hydrophobic agents will dissolve in lipophilic, nonaqueous solvents, the latter encompassing, for example, many organic solvents and lipidic fluids. Similarly, polar agents tend to dissolve in polar solvents, and nonpolar agents tend to dissolve in nonpolar solvents. Aqueous solvents comprise water and may additionally include components that are soluble or miscible in water, characteristics that may be useful or desirable for particular applications. Thus, aqueous solvents herein may include, but are not limited to, water, a water-ethanol or water-isopropanol admixture, ammonia water, a buffered aqueous medium, acidified water, basified water, and the like. Examples of organic solvents include, without limitation, hydrocarbons, and halogenated compounds such as carbon tetrachloride, ethers, ketones, amides, alcohols, polyhydric alcohols, amines, carboxylic acids, esters, lactams, nitriles, organic nitrates, and sulfides such as carbon disulfide. Typically, lipid solvents are organic as well.

After preparation, the drug-containing particles are packaged as is or in dosage forms. For pulmonary administration, the powders may be incorporated into a suitable inhaler. For oral delivery, pharmaceutical powders may be dissolved in water prior to administration, although capsules are preferred for oral administration. Suitable capsule materials may be either hard or soft, and as will be appreciated by those skilled in the art, typically comprise a tasteless, easily administered, and water soluble compound such as gelatin, starch, or a cellulosic material. See *Remington: The Science and Practice of Pharmacy*, Nineteenth Edition (Easton, Pa.: Mack Publishing Co., 1995), which describes materials and methods for preparing encapsulated pharmaceuticals. Each capsule will typically contain a therapeutically effective dose of the active agent. Alternatively, the dosage forms may contain less than a therapeutically effective dose in which case administration of two or more dosage forms would be required to achieve the therapeutically effective dose.

In preparing solid particles according to the invention, focused acoustic energy may be applied in a manner described in detail in U.S. Patent Application Publication No. 20020037579 to Ellson et al. FIG. 1 illustrates a focused acoustic ejection device that can be used in accordance with the foregoing method. The device is shown in simplified cross-sectional view. As with all figures referenced herein in which like parts are referenced by like numerals, FIG. 1 is not necessarily to scale, and certain dimensions may be exaggerated for clarity of presentation. The device 11 may include a single reservoir or a plurality of reservoirs. For simplicity, the device is illustrated as having a single reservoir 13 containing a solution 14 of a compound of interest dissolved in a solvent. The solution has a fluid surface indicated at 17. As shown, reservoir 13 is provided in a preferred axially symmetric form, having vertical wall 21 extending upward from circular reservoir base 25 and terminating at opening 29. However, other reservoir shapes may be used. When a plurality of reservoirs is employed, they may be of substantially identical construction so as to be substantially acoustically indistinguishable, but identical construction is not a requirement. In addition, a plurality of reservoirs may be provided as separate removable components but may, if desired, be fixed within a plate or other substrate. For example, the plurality of reservoirs may comprise individual wells in a well plate, optimally although not necessarily arranged in an array.

The device also includes an acoustic ejector 33, comprised of an acoustic radiation generator 35 for generating acoustic radiation, and a focusing means 37 for focusing the acoustic radiation at a focal point within the solution from which a droplet is to be ejected, near the fluid surface 17. As shown in FIG. 1, the focusing means 37 may comprise a single solid piece having a concave surface 39 for focusing acoustic radiation, although as discussed below, the focusing means may be constructed in other ways. The acoustic ejector 33 is thus adapted to generate and focus acoustic radiation so as to eject a droplet of fluid from fluid surface 17 when acoustically coupled to reservoir 13 and thus to solution 14. The acoustic radiation generator 35 and the focusing means 37 may function as a single unit controlled by a single controller, or they may be independently controlled, depending on the desired performance of the device. Typically, single ejector designs are sometimes preferred over multiple ejector designs for producing multiple droplets because single ejector designs tend to produce droplets and particles that are more uniform in size. In addition, it is generally easier to collect particles generated using a single ejector design. Thus, single ejector designs are more suited for laboratory or benchtop applications. Multiple-ejector designs, however, are advantageous in that they may be used to increase the rate of droplet and particle production. Thus, multiple-ejector designs are more for manufacturing and mass production applications, particularly for the pharmaceuticals industry.

Any of a variety of focusing means may be employed in conjunction with the present invention. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into the construction of commercially available acoustic transducers such as those manufactured by Panametrics, Inc. (Waltham, Mass.). In addition, Fresnel lenses are known in the art for directing acoustic energy at a predetermined focal distance from an object plane. (See, e.g., U.S. Pat. No. 5,041,849 to Quate et al.) Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane.

There are also a number of ways to acoustically couple the ejector 33 to the reservoir and thus to the fluid therein. One such approach is through direct contact, as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. However, this approach for acoustically coupling the focusing means to a fluid is generally undesirable for a number of reasons. For example, the transducer and/or the fluid coupling system are typically most costly components of acoustic systems. Submersion of these components may expose sensitive electronics typically contained therein to the fluid in the reservoir, thereby potentially compromising their performance. In addition, when the ejector is used to eject different fluids, repeated cleaning of the focusing means would be required in order to avoid cross-contamination. In such a case, fluid would adhere to the ejector as it is removed for cleaning, wasting material that may be costly or rare.

A preferred approach is to acoustically couple the ejector to the reservoir and the solution contained therein without contacting any portion of the ejector (e.g., the focusing means) with the solution. This overcomes the above-described disadvantages associated with submerged ejectors. Furthermore, should the ejector fail, a replacement ejector may be employed without disturbing the fluid in the reservoir. In such a case, the material and thickness of the reservoir should be such that acoustic radiation is transmitted therethrough and into the solution contained therein, so as to allow acoustic radiation from the ejector to be conveyed to the surface of the solution to be ejected. Typically, this involves providing a reservoir or well base that is sufficiently thin to allow acoustic radiation to travel therethrough without unacceptable dissipation. In addition, an ejector positioning means is provided for positioning the ejector in controlled and repeatable acoustic coupling with the reservoir to eject droplets therefrom without submerging the ejector therein, usually involving direct or indirect contact between the ejector and the external surface of each reservoir. When direct contact is used in order to acoustically couple the ejector to each reservoir, it is preferred that the direct contact be wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

Optimally, acoustic coupling is achieved between the ejector and the reservoir through indirect contact. In FIG. 1, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and the reservoir 13. Preferably, the fluid medium is substantially free of material having different acoustic properties than the fluid medium itself. The acoustic ejector 33 is positionable by means of ejector positioning means 43, shown below reservoir 13, in order to achieve acoustic coupling between the ejector and the reservoir through acoustic coupling medium 41. Once the ejector and the reservoir are in proper alignment, the acoustic radiation generator 35 is activated to produce acoustic radiation that is directed by the focusing means 37 to a focal point 47 near the fluid surface 17 of the first reservoir. As a result, droplet 49 is ejected from the fluid surface 17 into precipitation region 50, located immediately above fluid surface 17.

In order to ensure the accuracy of fluid ejection, it is often important to determine the precise location and orientation of the fluid surface from which a droplet is to be ejected with respect to the ejector. Otherwise, the ejected droplets may be improperly sized or travel in an improper trajectory. Thus, for optimal control over droplet ejection, the relative position between the ejector 33 and the fluid surface 17 in the reservoir should be controlled before each ejection event. Such precise control over droplet ejection may be achieved by activating the acoustic generator to produce a detection acoustic wave that travels to the fluid surface, which then gets reflected thereby as a reflected acoustic wave. Parameters of the reflected acoustic radiation are subsequently analyzed in order to assess the spatial relationship between the acoustic radiation generator and the fluid surface. Such an analysis involves the determination of the distance between the acoustic radiation generator and the fluid surface and/or the orientation of the fluid surface in relationship to the acoustic radiation generator, proving particularly useful when the fluid surface is nonplanar (e.g., convex or concave) due to surface forces associated with the contact between the fluid and the reservoir surface.

More particularly, the acoustic radiation generator may be activated so as to generate low energy acoustic radiation that is insufficiently energetic to eject a droplet from the fluid surface in the reservoir. This is typically accomplished by using an extremely short pulse (on the order of tens of nanoseconds) relative to that normally required for droplet ejection (on the order of microseconds). By determining the time it takes for the acoustic radiation to be reflected by the fluid surface back to the acoustic radiation generator and then correlating that time with the speed of sound in the fluid, the distance—and thus the fluid height—may be calculated. Of course, care must be taken in order to ensure that acoustic radiation reflected by the interface between the reservoir base and the fluid is discounted. It will be appreciated by those of ordinary skill in the art of acoustic microscopy that such a method employs conventional or modified sonar techniques. See U.S. patent application Ser. No. 10/175,374, entitled "Acoustic Control of the Composition and/or Volume of Fluid in a Reservoir," inventors Ellson and Mutz, filed Jun. 18, 2002.

Once the analysis has been performed, an ejection acoustic wave having a focal point near the fluid surface is generated in order to eject at least one droplet of the fluid, wherein the optimum intensity and directionality of the ejection acoustic wave is determined using the aforementioned analysis, optionally in combination with additional data. The "optimum" intensity and directionality are generally selected to produce droplets of consistent size and velocity. For example, the desired intensity and directionality of the ejection acoustic wave may be determined by using not only the spatial relationship assessed as above, but also geometric data associated with the reservoir, fluid property data associated with the fluid to be ejected, and/or historical droplet ejection data associated with the ejection sequence. In addition, the data may show the need to reposition the ejector so as to reposition the acoustic radiation generator with respect to the fluid surface, thus ensuring that the focal point of the ejection acoustic wave is near the fluid surface where desired. For example, if analysis reveals that the acoustic radiation generator is positioned such that the ejection acoustic wave cannot be focused near the fluid surface, the acoustic radiation generator is repositioned using vertical, horizontal, and/or rotational movement to allow appropriate focusing of the ejection acoustic wave.

Once ejected, the droplet 49 is subjected to a condition within precipitation region 50 that allows the compound of interest to be precipitated out of solution. Any number of means for creating such a precipitating condition may be used for the invention. As discussed above, exposing the droplet to an antisolvent will result in the precipitation of the compound of interest. This technique is discussed in detail in U.S. application Ser. Nos. 09/823,890 and 09/823,899. In addition, a compound of interest may be precipitated from a droplet when the droplet is subjected to a temperature and/or pressure change. Thus, the device may include other components that serve to heat or cool the ejected droplets, or to control the pressure of the environment into which the droplet is ejected. Design and construction of such temperature and/or pressure controlling means are known to one of ordinary skill in the art. By repeating the above-described technique, a plurality of particles of substantially identical size and composition may be formed.

Once the solid particle is formed, a means for collecting solid particles may be used. Any of number of particle collection technologies may be used in conjunction with the invention. As depicted in FIG. 1, for example, collector 51 may be used such that collector inlet 52 is positioned directly above the reservoir 13. Once the particle is formed, it may travel as a result of momentum from acoustic ejection into the collector inlet 51. Alternatively, a substrate having a surface adapted to retain particles may be used as a collector. In some instances, the particles may be collected in a reservoir of fluid. In such a case, the surface may be placed over the reservoir 13 in facing relationship to fluid surface 17. In some instances, gas flow may entrain the particle, thereby directing the particle to a collector. Furthermore, the particle may be electrostatically charged or subjected to electrostatic acceleration forces. Use of electrostatic charging in conjunction with acoustic ejection has been described in detail in U.S. Patent Application Publication No. 2002109084 to Ellson et al. Typically, it is preferred that the particles collected remain in an unagglomerated form such that each individual particle remains a discrete item that behaves in a manner similar to that of the other particles.

The device may include other components that enhance performance. For example, the device may further comprise a cooling means for lowering the temperature of a particle collection means (e.g., an upper surface within the contained enclosure) that is positioned above the reservoir. The device may also comprise a heating means for maintaining the fluid in the reservoir at a constant temperature, and, in combination with a pressurizing means, for maintaining the antisolvent in a supercritical state. Design and construction of such temperature maintaining means and pressurizing means are known to one of ordinary skill in the art. For many biomolecular applications, it is generally desired that the fluid containing the biomolecule be kept at a constant temperature without deviating more than about 1° C. or 2° C. therefrom. In addition, for a biomolecular fluid that is particularly heat sensitive, it is preferred that the fluid be kept at a temperature that does not exceed about 10° C. above the melting point of the fluid, preferably at a temperature that does not exceed about 5° C. above the melting point of the fluid. Thus, for example, when the biomolecule-containing fluid is aqueous, it may be optimal to keep the fluid at about 4° C. during ejection.

Figure 2:
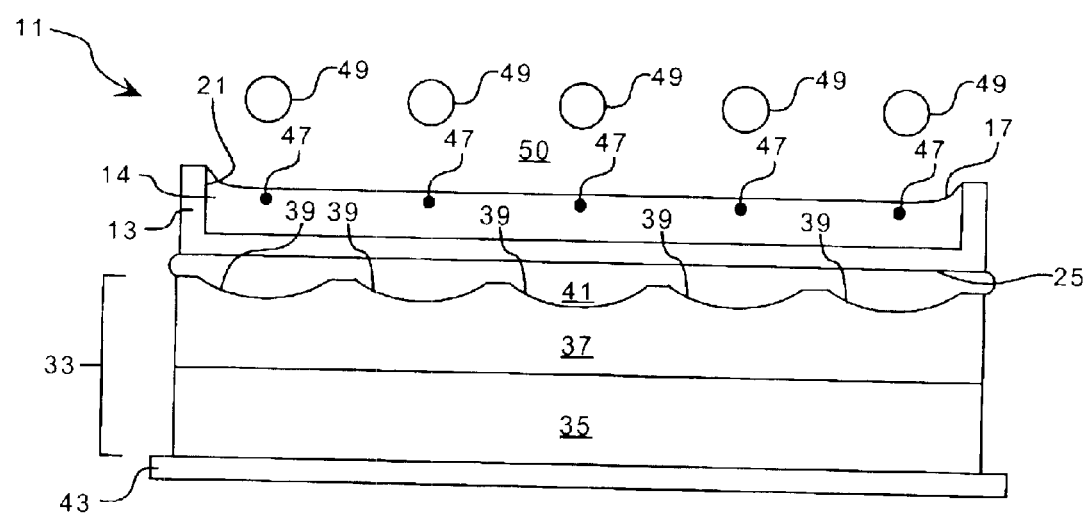
FIG. 2 is a schematic cross-sectional view a focused acoustic energy device useful in conjunction with the simultaneous preparation of a plurality of particles containing a compound of interest from a single reservoir.

FIG. 2 schematically illustrates in simplified cross-sectional view a focused acoustic energy device useful in conjunction with the simultaneous preparation of a plurality of solid particles from the same reservoir. In general, this device is similar to the device depicted in FIG. 1, and optional features described above may be employed with this device as well. As depicted in FIG. 2, the device 11 also has a single reservoir 13 containing a solution 14 of a compound of interest dissolved in a solvent. In addition, an acoustic ejector 33 is provided comprising an acoustic radiation generator 35 for generating acoustic radiation and a focusing means 37 for focusing the acoustic radiation. However, the focusing means is constructed to focus the acoustic radiation at a plurality of focal points within the solution from which a droplet is to be ejected, near the fluid surface 17. As shown in FIG. 2, the focusing means 37 may comprise a single solid piece having a plurality of substantially identical concave surfaces 39 for focusing acoustic radiation, but the focusing means may be constructed in other ways as discussed above. Focusing means with a plurality of multiple focusing elements are well known in the art.

An acoustic coupling medium 41 is placed between the ejector 33 and the base 25 of reservoir 13, and the acoustic radiation generator 35 is activated to produce acoustic radiation that is directed by the focusing means 37 to focal points 47 near the fluid surface 17 of the reservoir. The focal points 47 are near the portion of the fluid surface 17 that is substantially planar. As a result, droplets 49 are ejected from the fluid surface 17 into precipitation region 50, located immediately above fluid surface 17. Once ejected, the droplets 49 are subjected to a condition within precipitation region 50 that allows the compound of interest to be precipitated out of solution. The formed particles are then collected.

In another embodiment, the invention relates to a method for generating a solid particle coated with a compound of interest. This method also involves providing a reservoir as above, except that the reservoir additionally contains a discrete localized volume having a composition different from the composition of the solution. When focused acoustic radiation is applied, a droplet is ejected from the reservoir, wherein the droplet contains the discrete localized volume and the solution. Such use of acoustic energy to eject a discrete localized volume is generally described in U.S. Patent Application Publication No. 20020090720 to Mutz et al. and U.S. patent application Ser. No. 09/999,166 entitled "Spatially Directed Ejection of Cells from a Carrier Fluid," inventors Mutz and Ellson, filed Nov. 29, 2001. By subjecting the droplet to a condition that allows the compound of interest to precipitate out of solution onto the localized volume, a solid particle is formed coated with the compound of interest.

Typically, but not necessarily, the discrete localized volume is solid before, during, and/or after ejection from the solution. As a general rule, though, the core and/or coating should exhibit sufficient cohesiveness after ejection to provide the formed particle with sufficient mechanical integrity for ease in handling. For example, when the discrete localized volume is a gelled particle, the compound of interest may crystallize and harden on the surface of the gelled particle. In such case, the solid particle formed may be comprised of a hard crystalline shell encasing a gelled core region. Similarly, a core region comprising a viscous fluid may be formed in a like manner. Thus, the formed particle may take any of a number of forms depending on whether the inner core and/or the outer layer is subjected to certain processing techniques, e.g., gelling, drying, and etc.

The particle may also be subjected to polymerization techniques through the use of natural or synthetic monomeric units and/or polymers. U.S. Pat. No. 6,403,672 to Randolph et al., for example, describes a method of forming polymer particles by exposing at least one polymer precursor to photoradiation under conditions whereby particles are formed. The method also employs the use of a solvent in conjunction with a supercritical antisolvent fluid. In this patent, polymer precursors are defined as a molecule or portion thereof which can be polymerized to form a polymer or copolymer, and include any substance that contains an unsaturated moiety or other functionality that can be used in chain polymerization, or other moiety that may be polymerized in other ways. Exemplary precursors include monomers and oligomers that are capable of being polymerized by photoradiation, or those that may undergo radical and ionic polymerization. One of ordinary skill in the art will recognize that polymerization techniques are chemistry dependent and that experimentation may be needed to optimize the polymerization processes needed to produce optimal particles.

When the solid particle is prepared for use in a pharmaceutical application, the compound of interest may be any pharmaceutical agent as discussed above. In addition or in the alternative, the discrete localized volume may contain a pharmaceutical agent. For example, the pharmaceutical agent may be a pharmacologically active compound or an excipient. In addition, the compound of interest typically forms a coating having a thickness of no more than about 1 $\mu$m. Preferably, the coating has a thickness of no more than about 100 nm. Optimally, the coating has a thickness of about 10 nm to about 100 nm. Similarly, the discrete localized volume may have a size selected according to the desired size of the final solid particle formed. Thus, the volumetric ratio of the coating and the localized volume may vary. The outer coating typically occupies no more than about 50% of the total particle volume. In some instances, the outer coating occupies no more than about 10% of the total particle volume. When the localized volume occupies a large portion of the droplet volume, the outer coating may occupy no more than about 5% of the total particle volume. Thus, depending on the volumetric ratio of the fluid and the discrete volume of fluid ejected coating may a thickness no more than about 10% of the size of the particle. Depending on the precipitation condition, the compound of interest may form no subparticle larger than 10% of the size of the particle.

Regardless of whether a localized volume is contained in an ejected droplet, the droplet may be subjected to a particular condition that allows the compound to precipitate from solution at a plurality of loci. In some instances, a single solid particle is formed from the droplet. In such a case, the single solid particle formed may be comprised of a plurality of distinct regions, each region formed from the precipitation of the compound from solution. Assuming uniform nucleation and growth of the precipitation, the distinct regions are generally substantially identical in size. Alternatively, a plurality of solid particles is generated from the droplet. In such a case, the solid particles are preferably substantially identical in size. Typically, the size of the particle or particles generated is in the range of about 0.1 nm to about 1 μm. For certain applications, it is preferred that the size of the particle or particles generated be in the range of about 10 nm to about 100 nm.

Figure 3A:
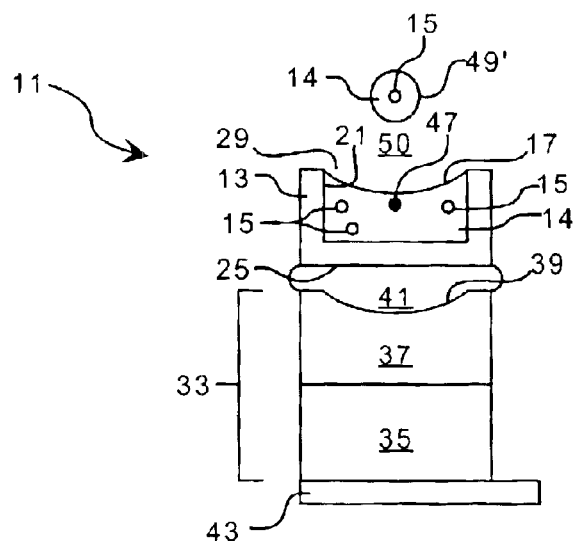
FIGS. 3A–3C, collectively referred to as FIG. 3, provides a schematic cross-sectional view a focused acoustic energy device useful for preparing a solid particle coated with a compound of interest formed as a result of multiple precipitations.
Figure 3B:
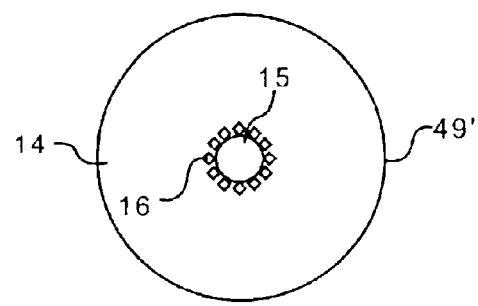
Figure 3C:
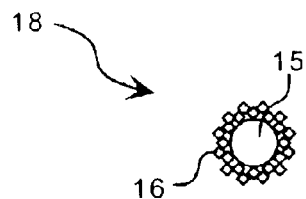

FIG. 3 schematically illustrates in simplified cross-sectional view an embodiment of the invention that uses a focused acoustic energy device for preparing a solid particle coated with a compound of interest, which formed as a result of multiple precipitations. As depicted in FIG. 3A, the device 11 also has a single reservoir 13 containing a solution 14 of a compound of interest dissolved in a solvent. In addition, the solution 14 also contains a plurality of discrete localized volumes 15. As shown, the localized volumes are solid and generally spherical in shape, but this is not a requirement. In addition, an acoustic ejector 33 is provided comprising an acoustic radiation generator 35 for generating acoustic radiation and a focusing means 37 for focusing the acoustic radiation. An acoustic coupling medium 41 is placed between the ejector 33 and the base 25 of reservoir 13, and the acoustic radiation generator 35 is activated to produce acoustic radiation that is directed by the focusing means 37 to a focal point 47 near the fluid surface 17 of the reservoir.

In order to ensure that the ejected droplet contains a spherical volume 15, the acoustic radiation generator 35 may be activated to produce an acoustic wave that is focused by the focusing means to direct the acoustic wave to a focal point 47 near fluid surface 17, with the amount of energy emitted being insufficient to eject fluid. This first emission of focused acoustic energy permits sonic detection of the presence of a sphere sufficiently close to the surface for ejection by virtue of reflection of acoustic energy. Acoustic energy is reflected due to the difference in acoustic impedance between the sphere and the solution carrier fluid. Methods for determining the position of the sphere by sonic detection are readily appreciated by those of ordinary skill in the art of acoustic microscopy and related arts. After the sphere is detected and localized, other factors, e.g. the proximity of the sphere to other spheres, may be considered before a decision to eject is made. Also, if no sphere is sufficiently close to the surface for ejection, the acoustic energy may be focused at progressively greater distances from the fluid surface until a sphere is located and driven closer to the surface by focused acoustic energy or other means. Once a sphere that is sufficiently close to the surface is located and has been determined to meet any other criteria for ejection, the acoustic radiation generator, as depicted in FIG. 3A, is activated to produce an acoustic wave that is focused by the focusing means to a focal point 47 near fluid surface 17, with the amount of energy being sufficient to eject a volume of fluid containing the sphere 15.

Once ejected, the droplet 49' travels away from the fluid surface 17 into precipitation region 50, located immediately above fluid surface 17. As depicted in FIG. 3B, the droplet 49' contains a solid sphere 15 encapsulated within the solution 14 containing the compound of interest. The droplet is subjected to a condition within precipitation region 50 that allows the compound of interest to be precipitated out of solution at a plurality of sites within the droplet 49' as a result of solvent evaporation from solution 14. Although multiple precipitations may occur spontaneously within a solution, the presence of a solid surface typically promotes nucleation of the dissolved compound. In some instances, such a solid surface may be formed with or altered to create additional nucleation sites on the surface. For example, the surface may undergo mechanical roughing. In addition, specialized coatings may be applied to the surface. Other methods in which a surface may be treated to promote crystallization are known in the art. Thus, as depicted, crystals 16 containing the compound of interest are formed on the surface of sphere 15. Once substantially all of the solvent has been removed from solution, as depicted in FIG. 3C, a solid particle 18 is formed comprising a spherical core 15 covered with a layer of crystals 16 of the compound of interest.

Furthermore, immiscible fluid technology may be advantageously employed with the inventive technology. For example, the invention provides a method for generating a solid particle comprised of different compounds of interest using immiscible fluids. A reservoir containing immiscible fluids is provided, wherein each fluid in the reservoir contains a different compound of interest. At least one of the fluids is comprised of a solution of the compound of interest dissolved in a solvent. Focused acoustic radiation is applied to at least one fluid contained in the reservoir in a manner effective to eject a droplet from the reservoir. The ejected droplet is comprised of the immiscible fluids. The droplet is then subjected to a condition that allows the dissolved compound to precipitate out of solution, thereby generating the solid particle. Immiscible fluid technologies such as those described in U.S. Patent Application Publication No. 20020037375 to Ellson et al. and in U.S patent application Ser. No. 10/112,693, entitled "Use of Immiscible Fluids in Droplet Ejection Through Application of Focused Acoustic Energy," inventors Ellson, Mutz and Foote, filed Mar. 29, 2002, may be adapted for use with the present invention.

Any one reservoir or droplet may contain two or more immiscible fluids, although often only two immiscible fluids are present. The immiscible fluids may have different viscosities, and one or more of the fluids may have a fairly high viscosity, e.g., at least about 10 cps, possibly at least about 100 cps. In one embodiment, for example, one of the fluids in a single reservoir may have a viscosity in the range of approximately 10 cps to approximately 10,000 cps, and another of the fluids therein may have a viscosity of less than about 0.3 cps.

In addition, various combinations of immiscible fluids may be contained in the reservoir. For example, each fluid may be comprised of a solution of a different compound of interest as a solute in a solvent. Alternatively, a compound of interest that is present in a fluid may not be a solute in a solvent, i.e., one or more of the fluids contained in the reservoir may be solvent free.

Furthermore, the immiscible fluids contained in the reservoir are typically comprised of a lower fluid layer and an upper fluid layer. Either or both of the lower and upper fluid layers may be comprised of a solution of a compound of interest as a solute in a solvent. Additionally, any of the fluids discussed above may be used as long as they are immiscible. Thus, for example, one of the fluids may be aqueous while another is nonaqueous. Lipidic materials, in particular, are generally immiscible with aqueous fluids.

By adjusting various parameters associated with focused acoustic ejection, the characteristics of the resultant droplets may be altered. In order to control the proportion of the immiscible fluids contained in each droplet, it is preferred that the proportion of immiscible fluids contained in each reservoir also be controlled. For example, in order to encapsulate a first fluid within a second, the lower layer should comprise the first fluid, and the upper layer should comprise the second, thus encapsulating fluid. When it is desired that a relatively large amount of a first fluid be encapsulated within a second, the thickness of the lower layer should be greater than the thickness of the upper layer. The thickness of the upper layer is preferably less than about 10% of the thickness of the lower layer, more preferably less than about 5% of the thickness of the lower layer, and typically in the range of about 0.1% to 5% of the thickness of the lower layer. However, the upper layer may, in some cases, comprise a molecular bilayer or even a molecular monolayer, e.g., when a very thin encapsulating coating is desired. Other factors that may have an effect on droplet production and the proportion of immiscible fluids within each droplet include, for example, the location of the focal point of the acoustic focusing means, the intensity of the applied acoustic energy, the interfacial surface energy between the fluids, and the like.

A number of techniques are known in the art for monitoring and or controlling the contents of a fluid reservoir. For example, U.S. patent application Ser. No. 10/175,374, entitled "Acoustic Control of the Composition and/or Volume of Fluid in a Reservoir," inventors Ellson and Mutz, filed Jun. 18, 2002, describes an apparatus and method that employs focused acoustic radiation to control the composition of fluid in a reservoir. The same or different acoustic unit may be used to acoustically monitor the fluid in and eject fluid out of the reservoir.

It should be noted that the performance of any acoustic monitoring means is related to the wavelength of the acoustic radiation used and the dimensions of the monitored object. Thus, in order to monitor the thickness of any particular fluid layer, it is desirable to employ acoustic radiation of a wavelength significantly shorter than the thickness of the fluid layer. Typically, the wavelength is no more than about 10% of the fluid layer thickness. Preferably, the wavelength is no more than about 5% of the fluid layer thickness. When a layer is particularly thin, nonacoustic monitoring means, e.g., measurement and/or metrology devices that employ electromagnetic radiation, may be used instead.

As the invention is particularly suited for pharmaceutical applications, it is typical that one, two, or more of the compounds of interest are pharmaceutical agents. For example, when a plurality of pharmaceutical agents is used, at least one pharmaceutical agent may be a pharmacologically active compound while another pharmaceutical agent serves as an excipient. The pharmaceutical agent may be provided in any number of forms, e.g., as a solute in a solution, as a solid particle in a suspension, a micelle in an emulsion, or as a vesicle in a dispersion.

Figure 4A:
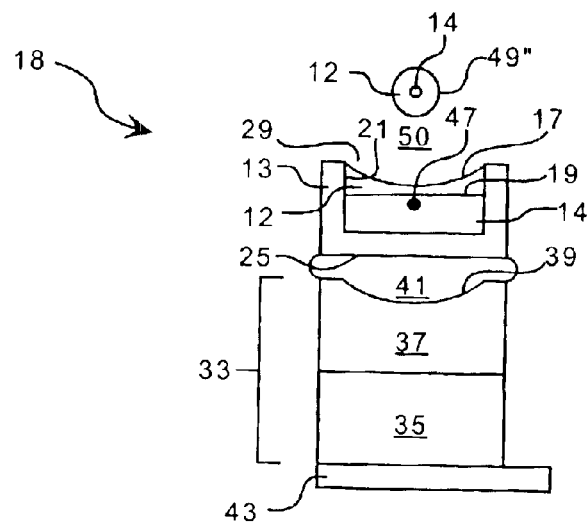
FIGS. 4A–4C, collectively referred to as FIG. 4, provides a schematic cross-sectional view a focused acoustic energy device useful in conjunction with the preparation of a particle using immiscible fluids.

FIG. 4 schematically illustrates in simplified cross-sectional view a focused acoustic energy device useful in conjunction with the preparation of a particle using immiscible fluids. As depicted in FIG. 4A, the device 11 has a reservoir 13 containing a lower fluid layer and an upper fluid layer. Although a two-phase system is illustrated and described, any reservoir of the invention may contain three or more immiscible fluids. The upper fluid layer has a fluid surface indicated at 17, and the interface between the upper fluid layer and the lower fluid layer is indicated at 19. As depicted, the lower fluid layer includes a solution 14 containing a first compound of interest as a solute. The upper fluid layer contains a polymerizable fluid 12 that is immiscible with the solution 14 in the lower layer. While the layers of immiscible fluids may exhibit a uniform thickness, only the lower layer is depicted having a uniform thickness. The upper layer does not exhibit a uniform thickness, and the fluid surface 17 is curved. An aperture region corresponding to the region of the upper layer having a localized thickness minimum is located at the center of the upper fluid layer. The aperture region tends to be of high dimensional stability.

In operation, the acoustic ejector 33 is positionable by means of ejector positioning means 43, shown below reservoir 13, in order to achieve acoustic coupling between the ejector and the reservoir through acoustic coupling medium 41. Once the ejector, the reservoir, and the substrate are in proper alignment, the acoustic radiation generator 35 is activated to produce acoustic radiation that is directed by the focusing means 37 to a focal point 47 near the interface between the upper layer and the lower layer. The acoustic energy is delivered in sufficient quantity to form a droplet 49" of the solution 14 from the lower layer coated with the fluid 12 from the upper layer. Since the droplet is formed from the ejection of solution 14 through the aperture region of the upper layer, the exterior coating of fluid 12 on droplet 49" is thin. In some instances, the coating may represent a molecular monolayer.

Figure 4B:
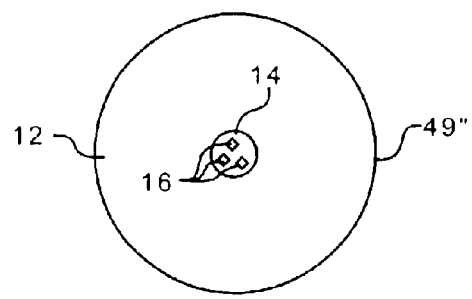
Figure 4C:
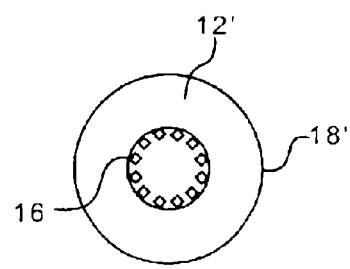

Once ejected, the ejected droplet 49" travels away from the fluid surface 17 into precipitation region 50, located immediately above fluid surface 17. As depicted in FIG. 4B, the outer layer fluid 12 of the droplet 49" is polymerized, and the compound of interest is to be precipitated out of solution at a plurality of sites within the droplet 49. Thus, as depicted, a plurality of crystals 16 of the compound of interest is formed within the solution 14. Once substantially all of the solvent has been removed from solution, as depicted in FIG. 4C, a hollow particle 18' is formed comprising a polymerized spherical outer layer 12 having an interior surface covered with a layer of crystals 16 of the compound of interest.

As with other embodiments described herein, this embodiment typically employs RF energy at frequencies of 200 to 400 MHz. However, the actual frequency used depends on various experimental parameters such as the speed of sound in the therapeutic agent solution, the F-number of the acoustic focusing means, the position of focal spot with respect to the fluid layers, and the power received at the focal spot. Similarly, geometric concerns such as the size of the reservoirs and the thickness of fluid layers may have an effect on the optimal frequency for ejection.

Thus, the invention also provides a system for generating solid particles of a plurality of compounds of interest. The system is similar to that described in detail in U.S. Patent Application Publication No. 20020037579 to Ellson et al. A reservoir is provided containing a solution of a first compound of interest as a solute in a solvent and a second compound of interest. The system also includes an acoustic ejector comprising an acoustic radiation generator for generating acoustic radiation and a focusing means for focusing the acoustic radiation at a focal point within the solution in the reservoir so as to eject a droplet therefrom. The ejector is positioned in acoustic coupling relationship to the reservoir. In addition, the second compound of interest is contained in a fluid that is immiscible with the solution and/or in a discrete localized volume within the solution. Optionally, there is a means for subjecting the droplet to a condition that allows the first compound of interest to precipitate out of solution.

The material used in the construction of any reservoir for use with the invention must be compatible with the fluids contained therein. Thus, if it is intended that the reservoirs or wells contain a particular organic solvent, polymers that dissolve or swell in that solvent would be unsuitable for use in forming the reservoirs or well plates. For water-based fluids, a number of materials are suitable for the construction of reservoirs and include, but are not limited to ceramics (such as silicon oxide and aluminum oxide), metals (such as stainless steel and platinum), and polymers (such as polyester and polytetrafluoroethylene).

For the industrial and/or large-scale production context, a large volume but shallow reservoir is typically used with one or more ejectors to eject droplets from a plurality of loci. In such a case, the fluid contained in the reservoir typically exhibits a free surface having dimensions that greatly exceeds the depth of the fluid. FIG. 2 provides an example of such a reservoir configuration. In such a case, the focused acoustic radiation has a characteristic wavelength. The distance between the base of the reservoir and the free surface of the fluid contained in the reservoir is typically no more than 50 times the characteristic wavelength of the acoustic radiation employed. Preferably, the distance is no more than 10 times the characteristic wavelength of the acoustic radiation. In addition, for such a reservoir configuration, the focusing means typically has an F-number of less than 2, preferably an F-number of about 1 or less. To illustrate, it should be noted that when acoustic radiation of about 200 MHz or greater is used, a focusing means having a F-number closer to 1 may generally be used with reservoirs having a shallow depth. For frequencies in the 300 MHz range and fluids with sound speeds of 1500 m/s, the acoustic radiation should have a wavelength about 5 $\mu$m. Hence, a reservoir having a 100 $\mu$m depth would be adequate from which to form drops for many fluids and F-number lenses.

The device of the invention enables ejection of droplets at a rate of at least about 1,000,000 droplets per minute from the same reservoir, and at a rate of at least about 100,000 drops per minute when the ejector has to be moved between each ejection. When a single ejector is used to eject fluid from a fluid surface, it is preferred that the surface is substantially undisturbed before the application of focused acoustic radiation. Current positioning technology allows for the ejector positioning means to move from site associated with an undisturbed surface to another quickly and in a controlled manner.

For small laboratory applications, many well plates suitable for laboratory use are commercially available and may contain, for example, 96, 384, 1536, or 3456 wells per well plate. Manufacturers of suitable well plates for use in the inventive device include Corning, Inc. (Corning, N.Y.) and Greiner America, Inc. (Lake Mary, Fla.). However, the availability of such commercially available well plates does not preclude the manufacture and use of custom-made well plates containing at least about 10,000 wells, or as many as 100,000 wells or more. In addition, for multiple reservoir systems, it is preferable that the center of each reservoir be located not more than about 1 centimeter, preferably not more than about 1 millimeter, and optimally not more than about 0.5 millimeter from another reservoir center Because of the precision that is enabled by the inventive technology, the device may be used in a laboratory setting to eject droplets from a reservoir adapted to contain no more than about 100 nanoliters of fluid, preferably no more than 10 nanoliters of fluid. In certain cases, the ejector may be adapted to eject a droplet from a reservoir adapted to contain about 1 to about 100 nanoliters of fluid. This is particularly useful when the fluid to be ejected contains rare or expensive biomolecules, wherein it may be desirable to eject droplets having a volume of about 1 picoliter or less (e.g., droplets having a volume in the range of about 0.25 picoliters to about 1 picoliter). To ensure that substantially the entire volume of fluid in a reservoir is used, acoustic focusing means having higher F-numbers may be used. In some instances, the focusing means may have an F-number of at least about 2. Focusing means having an F-number of at least about 3 are preferred for reservoirs with a higher height to diameter aspect ratio. One of ordinary skill in the art will be able to adapt the technologies discussed in U.S. Pat. No. 6,416,164 to Stearns et al. for use with the present invention. Other aspects of useful acoustic ejection technology for laboratory use are described in U.S. Patent Application Publication No. 20020037579 to Ellson et al.

Variations of the present invention will be apparent to those of ordinary skill in the art. For example it is well known that certain additives may be used to promote or inhibit precipitation. As a result, such additives may affect crystal nucleation and growth, macrostep formation, agglomeration and composition of crystal precipitate. For example, "tailor-made" additives may be used to interact in very specific ways with selected faces of crystalline materials. These additives are designed to contain some chemical groups or moieties that mimic the solute molecule and are thus readily adsorbed at growth sites on the crystal surface. In addition, crystal habit or morphology may be controlled through selective use of certain additives. Similarly, control over impurities may also achieve some or all of these effects.

It is to be understood that, while the invention has been described in conjunction with the preferred specific embodiments thereof, the foregoing description is intended to illustrate and not limit the scope of the invention. Other aspects, advantages, and modifications will be apparent to those skilled in the art to which the invention pertains.

All patents, patent applications, journal articles, and other references cited herein are incorporated by reference in their entireties.

The following examples are put forth so as to provide those of ordinary skill in the art with a complete disclosure and description of how to implement the invention, and are not intended to limit the scope of what the inventors regard as their invention.

EXAMPLE 1

This example demonstrates the use of focused acoustic ejection technology in generating a particle from a droplet of immiscible fluids. A reservoir is provided containing two layers of immiscible fluid. The upper layer contains a coating fluid comprised of a natural phospholipid such as sphingomyelin, phosphatidylethanolamine, or phosphatidylcholine, and the lower layer contains an aqueous solution of a therapeutic agent near its solubility limit. Focused acoustic energy having a wavelength comparable to the desired particle size is directed to a focal point near the interface between the upper and lower layers. As a result, a droplet of the aqueous solution coated with the coating fluid is ejected. The droplet is then rapidly cooled to 5° C. to force a rapid nucleation at multiple locations within the droplet and subsequent crystallization of the therapeutic agent. Optionally, at least a portion of the solvent is removed from the particle interior to complete crystallization. Such solvent removal also serves to prevent redissolution of the crystals when the particle returns to its original temperature.

EXAMPLE 2

Focused acoustic ejection technology is used in the manner described in Example 1, except that the upper layer contains a synthetic coating fluid comprised of a monomer or a monomer/polymer blend (e.g., methyl methacrylate or methyl methacrylate/polymethyl methacrylate blend) and photoinitiator. Once the droplet has been rapidly cooled to 5° C. to force a rapid nucleation at multiple locations within the droplet, the droplet is exposed to light of an appropriate wavelength. As a result, the therapeutic agent is crystallized within a poly(methyl methacrylate) shell. As a result, a more rigid overall particle structure is formed. The particle is then stored in a dry gas environment to remove any internal solvent.

EXAMPLE 3

This example demonstrates the use of focused acoustic ejection technology in generating a particle useful for the behavior of two-dimensional protein crystallization the surfaces of giant lipid bilayer vesicles. Such vesicles are described in Menger et al. (1998), "Chemistry and Physics of Giant Vesicles as Biomembrane Models," *Curr. Opin. Chem. Biol.*, 2: 726–732, in Korlach et al. (1999), "Characterization of Lipid Bilayer Phases by Confocal Microscopy and Fluorescence Correlation Spectroscopy," *PNAS USA* 96:8461–8466, and in Dietrich et. al. (2001), "Lipid Rafts Reconstituted in Model Membranes," *Biophysical J.* 60:1417–1428. Focused acoustic ejection technology is used in the manner described in Example 1, except that the upper layer contains a lipid and the lower fluid is comprised of an aqueous solution of a compound such as streptavidin that is both hydrophobic and hydrophilic. Focused acoustic energy is directed to a focal point near the interface between the upper and lower layers. As a result, a droplet is ejected having a size of approximately 20 $\mu$m and comprising the aqueous solution coated with the lipid. Once ejected, the droplet forms a giant lipid bilayer vesicle of about 20 microns in diameter.

Once formed, the compound is subjected to a precipitation condition such that it nucleates at a plurality of nucleation sites at the interface between the aqueous solution and the lipid coating. The resultant compound crystals grow and form localized domains on the outer vesicle surface. The rigidity of the compound crystals distorts the vesicle shapes, and the vesicles exhibit either faceted spherical or spheroidal shapes.

We claim:

1. A method for generating solid particles of substantially identical size, the method comprising:
   (a) applying focused acoustic radiation to a solution in a reservoir in a manner effective to eject a droplet of the solution from the reservoir, wherein the solution is comprised of a compound of interest dissolved in a solvent;
   (b) subjecting the droplet to a condition that allows the compound to precipitate out of solution, thereby forming a solid particle;
   (c) repeating steps (a) and (b) so as to form solid particles of substantially identical size.

2. The method of claim 1, wherein step (a) comprises applying focused acoustic radiation to the solution in the reservoir at a plurality of loci so as to eject droplets therefrom.

3. The method of claim 2, wherein droplets are ejected from the loci substantially simultaneously.

4. The method of claim 2, wherein droplets are ejected at different times.

5. The method of claim 1, wherein step (b) comprises exposing the droplet to an antisolvent.

6. The method of claim 5, wherein the antisolvent is a supercritical fluid.

7. The method of claim 5, wherein the antisolvent is gaseous.

8. The method of claim 1, wherein step (b) comprises heating the droplet.

9. The method of claim 1, wherein step (b) comprises cooling the droplet.

10. The method of claim 1, wherein step (b) comprises exposing the droplet to a reduced pressure.

11. The method of claim 1, wherein step (b) comprises crystallizing the compound.

12. The method of claim 1, wherein step (b) comprises allowing the compound to chemically react with another compound in the droplet.

13. The method of claim 1, wherein step (b) comprises allowing the compound to polymerize.

14. The method of claim 1, wherein the particles generated are substantially free of solvent.

15. The method of claim 1, wherein the generated particles contain a fluid.

16. The method of claim 1, wherein the reservoir contains no more than about 100 nanoliters of the solution.

17. The method of claim 16, wherein the reservoir contains no more than about 10 nano liters of the solution.

18. The method of claim 1, wherein the applied focused acoustic radiation has a characteristic wavelength and travels a distance of no more than 50 times the characteristic wavelength through the solution before a droplet is ejected from the reservoir.

19. The method of claim 18, wherein the distance traveled by the acoustic radiation is no more than 10 times the characteristic wavelength of the acoustic radiation.

20. The method of claim 1, wherein the solution is substantially saturated with the compound of interest.

21. The method of claim 1, wherein the solvent is aqueous.

22. The method of claim 1, wherein the solvent is non-aqueous.

23. The method of claim 22, wherein the solvent is organic.

24. The method of claim 1, wherein the solvent is polar.

25. The method of claim 1, wherein the solvent is nonpolar.

26. The method of claim 1, wherein the compound is a biomolecule.

27. The method of claim 1, wherein the compound is a pharmaceutical agent.

28. The method of claim 27, wherein the pharmaceutical agent is hydrophilic.

29. The method of claim 27, wherein the pharmaceutical agent is lipophilic.

30. The method of claim 27, wherein the pharmaceutical agent is peptidic.

31. The method of claim 27, wherein the pharmaceutical agent is a respiratory drug.

32. The method of claim 31, wherein the respiratory drug is selected from the group consisting of anti-inflammatory corticosteroids, bronchodilators, and mixtures thereof.

33. The method of claim 27, wherein the pharmaceutical agent is a diagnostic agent.

34. The method of claim 27, wherein the pharmaceutical agent is solublized and/or stabilized by a membrane lipid.

35. The method of claim 34, wherein the membrane lipid is selected from the group consisting of sphingomyelin, phosphatidylethanolamine, phosphatidyicholine, and combinations thereof.

36. The method of claim 1, wherein the focused acoustic radiation is applied using a focusing means having an F-number of less than 2.

37. The method of claim 36, wherein the focused acoustic radiation is applied using a focusing means having an F-number less than 1.

38. A method for generating a solid particle coated with a compound of interest, the method comprising:
  (a) providing a reservoir containing a discrete localized volume and a solution comprised of the compound of interest dissolved in a solvent, wherein the discrete localized volume has a composition different from that of the solution;
  (b) applying focused acoustic radiation to the solution in a manner effective to eject a droplet from the reservoir, wherein the droplet contains the discrete localized volume and the solution;
  (c) subjecting the droplet to a condition that allows the compound of interest to precipitate out of solution onto the localized volume, thereby forming a solid particle coated with the compound of interest.

39. The method of claim 38, wherein the discrete localized volume contains a pharmaceutical agent.

40. The method of claim 39, wherein the pharmaceutical agent is a pharmacologically active compound.

41. The method of claim 39, wherein the pharmaceutical agent is an excipient.

42. The method of claim 38, wherein the discrete localized volume is a solid.

43. The method of claim 38, wherein the size of the solid particle formed is in the range of about 0.1 nm to about 10 µm.

44. The method of claim 43, wherein the size of the solid particle formed is in the range of about 2 µm to about 7 µm.

45. The method of claim 38, wherein the compound of interest forms a coating having a thickness of no more than about 1 µm.

46. The method of claim 45, wherein the compound of interest forms a coating having a thickness of no more than about 100 nm.

47. The method of claim 46, wherein the compound of interest forms a coating having a thickness of about 10 nm to about 100 nm.

48. The method of claim 38, wherein the compound of interest forms a coating having a thickness no more than about 10% of the size of the particle.

49. The method of claim 38, wherein the compound of interest forms no subparticle larger than 10% of the size of the particle.

50. A method for generating a solid particle comprised of different compounds of interest, the method comprising:
  (a) providing a reservoir containing immiscible fluids, wherein each fluid in the reservoir contains a different compound of interest, and at least one fluid is comprised of a solution of a compound of interest dissolved in a solvent;
  (b) applying focused acoustic radiation to at least one fluid contained in the reservoir in a manner effective to eject a droplet from the reservoir, wherein the droplet is comprised of at least two of the immiscible fluids;
  (c) subjecting the droplet to a condition that allows the dissolved compound to precipitate out of solution, thereby generating the solid particle.

51. The method of claim 50, wherein the each fluid is comprised of a solution of a different compound of interest as a solute in a solvent.

52. The method of claim 50, wherein the compound of interest contained in at least one fluid is not a solute in a solvent.

53. The method of claim 50, wherein at least one fluid is solvent free.

54. The method of claim 52, wherein at least one of the compounds of interest is a pharmaceutical agent.

55. The method of claim 54, wherein at least two of the compounds of interest are pharmaceutical agents.

56. The method of claim 55, wherein at least one pharmaceutical agent is a pharmacologically active compound and another pharmaceutical agent is an excipient.

57. The method of claim 50, wherein the immiscible fluids contained in the reservoir are comprised of a lower fluid layer and an upper fluid layer.

58. The method of claim 57, wherein the lower fluid layer is comprised of a solution of a compound of interest as a solute in a solvent.

59. The method of claim 57, wherein the upper fluid layer is comprised of a solution of a compound of interest as a solute in a solvent.

60. The method of claim 50, wherein one of the fluids is aqueous and another of the fluids is nonaqueous.

61. The method of claim 60, wherein the nonaqueous fluid is comprised of a lipidic material.

62. The method of claim 50, wherein the at least one solute compound is biomolecule.

63. The method of claim 50, wherein the at least one solute compound is a pharmaceutical agent.

64. The method of claim 50, wherein the solid particle generated is comprised of an outer region encapsulating a core region.

65. The method of claim 64, wherein the outer region is comprised of the at least one solute compound.

66. The method of claim 64, wherein the core region is comprised of the at least one solute compound.

67. The method of claim 64, wherein the outer region occupies no more than about 50% of the total particle volume.

68. The method of claim 67, wherein the outer region occupies no more than about 10% of the total particle volume.

69. The method of claim 68, wherein the outer region occupies no more than about 5% of the total particle volume.

70. The method of claim 50, further comprising, after step (a) and before step (b), acoustically assessing the composition, volume and/or depths of the fluids in the reservoir.

71. A method for generating at least one solid particle, each containing a compound of interest, the method comprising:
  (a) applying focused acoustic radiation to a solution in a reservoir in a manner effective to eject a droplet of the solution from the reservoir, wherein the solution is comprised of a compound of interest dissolved in a solvent; and
  (b) subjecting the droplet to a condition that allows the compound to precipitate from the solution at a plurality of loci, thereby generating at least one solid particle.

72. The method of claim 71, wherein a single solid particle is formed from the droplet.

73. The method of claim 72, wherein the single solid particle is comprised of a plurality of distinct regions, and each region is formed from the precipitation of the compound from solution.

74. The method of claim 73, wherein the distinct regions are substantially identical in size.

75. The method of claim 71, wherein a plurality of solid particles is generated from the droplet.

76. The method of claim 75, wherein the solid particles are substantially identical in size.

77. The method of claim 71, wherein the size of the at least one particle is in the range of about 0.1 nm to about 1 $\mu$m.

78. The method of claim 77, wherein the size of the at least one particle is in the range of about 10 nm to about 100 nm.

79. The method of claim 71, wherein the reservoir further contains a discrete localized volume having a composition different from the composition of the solution, and the ejected droplet contains the discrete localized volume.

80. The method of claim 79, wherein the compound of interest is deposited onto a surface of the localized volume.

81. The method of claim 71, wherein the reservoir further contains a fluid that is immiscible with the solution.

82. A system for generating solid particles of a plurality of compounds of interest, comprising:

a reservoir containing a solution of a first compound of interest as a solute in a solvent and a second compound of interest, wherein the second compound of interest is contained in a fluid that is immiscible with the solution and/or in a discrete localized volume within the solution;

an acoustic ejector comprising an acoustic radiation generator for generating acoustic radiation and a focusing means for focusing the acoustic radiation at a focal point within the solution in the reservoir so as to eject a droplet therefrom; and a means for positioning the ejector in acoustic coupling relationship to the reservoir.

83. The system of claim 82, further comprising a means for subjecting the droplet to a condition that allows the first compound of interest to precipitate out of solution.

* * * * *